United States Patent [19]

Gorfine

[11] Patent Number: 5,504,117

[45] Date of Patent: Apr. 2, 1996

[54] PHARMACOLOGIC PREPARATION FOR THE TREATMENT OF ANAL DISORDERS

[75] Inventor: Stephen R. Gorfine, New York, N.Y.

[73] Assignee: Neptune Pharmaceutical Corporation, Kansas City, Mo.

[21] Appl. No.: 250,555

[22] Filed: May 27, 1994

[51] Int. Cl.$^6$ .................................................. A61K 31/04
[52] U.S. Cl. .................. 514/742; 514/470; 514/740; 514/171; 514/179; 514/312; 514/882
[58] Field of Search .................................. 514/171, 179, 514/312, 742, 882, 470, 740

[56] References Cited

U.S. PATENT DOCUMENTS

| 814,408 | 3/1906 | Steele . | |
|---|---|---|---|
| 2,840,080 | 12/1956 | Clark | 128/296 |
| 4,118,480 | 10/1978 | Williams | 424/131 |
| 4,292,299 | 9/1981 | Suzuki et al. | 424/16 |
| 5,059,603 | 10/1991 | Rubin | 514/264 |
| 5,183,663 | 2/1993 | Greiner | 424/443 |

FOREIGN PATENT DOCUMENTS

| PM6395 | 7/1994 | Australia . |
| PM0971 | 3/1995 | Australia . |
| PM4247 | 3/1995 | Australia . |
| 7701135 | 2/1977 | South Africa . |
| 77/1135 | 4/1978 | South Africa . |
| 95/06466 | 8/1994 | WIPO . |

OTHER PUBLICATIONS

Rattan et al., "Nitric Oxide Pathway in Rectoanal Inhibitory Reflex of Oppossum Internal Anal Sphincter," Gastroenterology, vol. 103, pp. 43–50, 1992.

Rattan et al., "Role of Nitric Oxide as a Mediator of Internal Anal Sphincter Relaxation," from article Nitric Oxide as Gut Smooth Muscle Inhibitory Mediator, American Journal of Physiology, pp. G107–G112, 1992.

O'Kelly et al., "Nerve Mediated Relaxation of the Human Internal Anal Sphincter: The Role of Nitric Oxide," Gut, vol. 34, pp. 689–693, 1993.

Chakder et al., "Release of Nitric Oxide by Activation of Nonadrenergic Noncholinergic Neurons of Internal Anal Sphincter," American Journal Physiology, vol. 264, pp. G7–G12, 1993.

Loder et al., "Reversible Chemical Sphincterotomy by Local Application of Glyceryl Trinitrate," British Journal of Surgery, vol. 81, pp. 1386–1389, 1994.

Schouten, et al., "Pathophysiological Aspects and Clinical Outcome of Intra–anal Application of Isosorbide–di–Nitrate in Patients with Chronic Anal Fissure", Dis Colon Rectum, Apr., 1985, p. 18.

Loder, et al., "Topical Application of a Nitric Oxide Donor Reduces Internal Anal Sphincter Tone: Therapeutic Implications" Gastroenterology, 93 104 A544, Apr., 1993 (Abstract).

Loder, et al., "Topical Application of a Nitric Oxide Donor Reduces Internal Anal Sphincter Tone: Therapeutic Implications", Gut 1993, 34 S25, Apr., 1993. (Abstract).

Jensen, "Treatment of First Episodes of Acute Anal Fissure: Prospective Randomised Study of Lignocaine Ointment Versus Hydrocortisone Ointment or Warm Sitz Baths Plus Bran", 1986, Br. Med. J. 292 (6529) 1167–9.

Watson, et al. "Glyceryl Trinitrate and Anal Fissure: Resistance to Endogenous Nitric Oxide and Tachyphylaxis", Diseases of the Color & Rectum, vol. 38, No. 4, Apr., 1995, p. 29.

Primary Examiner—Marianne M. Cintins
Assistant Examiner—Minna Moezie
Attorney, Agent, or Firm—Shook, Hardy & Bacon

[57] ABSTRACT

A medical preparation for treating anal disorders comprises an effective amount of a nitric oxide donor, preferably an organic nitrate. The preparation may be in the form of an ointment that is applied to affected tissue at least once daily.

26 Claims, No Drawings

PHARMACOLOGIC PREPARATION FOR THE TREATMENT OF ANAL DISORDERS

FIELD OF THE INVENTION

This invention relates to the treatment of certain benign anal conditions. More particularly, the invention relates to a method of treating anal fissure, anal ulcer, hemorrhoidal disease, and levator spasm with a medication comprising an effective amount of organic nitrate or other similar substance capable of acting as a nitric oxide donor.

BACKGROUND OF THE INVENTION

Anal fissure (or fissure-in-ano), anal ulcer, acute hemorrhoidal disease, and levator spasm (proctalgia fugax) are common, benign conditions of the anal canal which affect men and women. An anal fissure or ulcer is a tear or ulcer of the mucosa or lining tissue of the distal anal canal. An anal fissure/ulcer can be associated with other systemic or local diseases, but it is more frequently present as an isolated finding. The typical, idiopathic fissure or ulcer is confined to the anal mucosa, and usually lies in the posterior midline, distal to the dentate line. The person with an anal fissure or ulcer suffers from anal pain and bleeding, more pronounced during and after bowel movements.

Hemorrhoids are specialized vascular areas lying subjacent to the anal mucosa. Symptomatic hemorrhoidal disease is manifest by bleeding, thrombosis or prolapse of the hemorrhoidal tissues. Men and women are affected. Most commonly, internal hemorrhoidal tissue bulges into the anal canal during defecation causing bleeding. As the tissue enlarges, prolapse pain, thrombosis, and bleeding can ensue. Thrombosis of internal or external hemorrhoids is another cause of pain and bleeding.

Levator spasm (or proctalgia fugax) is a condition of unknown etiology affecting women more frequently than men. This syndrome is characterized by spasticity of the levator ani muscle, a portion of the anal sphincter complex. The patient suffering from levator spasm complains of severe, episodic rectal pain. Physical exam may reveal spasm of the puborectalis muscle. Pain may be reproduced by direct pressure on this muscle. Bleeding is not associated with this condition.

The underlying causes of these problems are poorly understood. However, all of these disorders are associated with a relative or absolute degree of anal sphincter hypertonicity. In the case of anal fissure/ulcer the abnormality appears to be an as yet unidentified problem of the internal and sphincter muscle. The internal sphincter is a specialized, involuntary muscle arising from the inner circular muscular layer of the rectum. Intra-anal pressure measurements obtained from people suffering from typical anal fissure/ulcer disease show an exaggerated pressure response to a variety of stimuli. The abnormally high intra-anal pressure is generated by the internal sphincter muscle. The abnormally elevated intra-anal pressure is responsible for non-healing of the fissure/ulcer and the associated pain.

An abnormal pressure response in the anal canal has also been observed in people suffering from symptomatic hemorrhoidal disease. Elevated intra-anal pressures may be a major etiologic factor in the development of this condition. It is postulated that the pain associated with acute hemorrhoidal disease is caused in part by spasm of the internal anal sphincter muscle. Similarly, the pain associated with levator spasm is induced by the muscle spasm itself.

Various therapies have been devised to treat these problems. Typical, non-surgical therapy includes bulk laxatives and sitz baths. Sitz baths are helpful because they induce relaxation of the anal sphincter mechanism. Topical anal therapy is used to promote healing, relieve pain, and reduce swelling and inflammation. Many preparations have been tried, including those containing local anesthetics, corticosteroids, astringents, and other agents. None of these preparations adequately addresses the underlying problem of sphincter spasm. Consequently, none has been show conclusively to favorably alter the time course to healing or to reliably ameliorate associated pain.

Those cases of anal fissure/ulcer or hemorrhoids recalcitrant to medical therapy are often referred for surgical treatment. In keeping with the proposed etiology of anal fissure/ulcer, the current standard surgical procedure for treatment of anal fissure is lateral internal anal sphincterotomy. In this procedure, the internal anal sphincter muscle is partially cut, thereby reducing the intra-anal pressure. The lowered pressure allows the fissure/ulcer to heal and also relieves the associated pain. Surgical hemorrhoidectomy removes the redundant hemorrhoidal tissue. Many surgeons will perform concomitant limited internal anal sphincterotomy to lower anal canal pressure. There is no successful surgical treatment for levator spasm.

Over the past five years a third component of the autonomic nervous system, the enteric nervous system (ENS), has been described and elucidated. This neural network innervates the gut continuously from esophagus to anus. It is composed of enteric neurons and the processes of extrinsic efferent and afferent neurons of the traditional autonomic system. This system regulates the motor and secretory function of the gut.

The most remarkably feature of the ENS is the diversity of chemical messengers that enteric neurons contain and release. In addition to acetylcholine and norepinephrine, various peptide and non-peptide substances have been identified which appear to function as neurotransmitters. Most recently, nitric oxide (NO) has been identified as an inhibitory transmitter to muscle. Rattan, Chakder, O'Kelly, and others have shown that NO mediates the anorectal inhibitory reflex in animals and man. See, Rattan et al., S. Nitric oxide pathway in rectonal inhibitory reflex of opossum internal anal sphincter, *Gastroenterology* 103:43–50, 1992; Chakder et al., Release of nitric oxide by activation of nonadrenergic noncholinergic neurons of internal anal sphincter, *Am. J. Physiol.* 264:G7–12, 1993; and O'Kelly, et al., Nerve mediated relaxation of the human internal anal sphincter: The role of nitric oxide. *Gut* 34:689–693, 1994, each of which is incorporated herein by reference.

Organic nitrates such as nitroglycerin (the trinitrate, NTG), isosorbide dinitrate, isosorbide mononitrate, erythrityl tetranitrate, and others have been used for decades in the clinical setting of angina pectoris. These agents act as physiologic nitric oxide donors. The use of organic nitrates has not been previously proposed for the treatment of anal disease.

Corticosteroids such as hydrocortisone, have been used for various benign anal disorders for many years. Studies of the effectiveness of this treatment have shown some benefit, but not in a reproducible or significant fashion. It has not been heretofore known to use hydrocortisone in combination with organic nitrates for treatment of anal diseases.

Topical anesthetics such as dibucaine, lidocaine, pramoxine, and others have been used for treatment of anal pain. It has not been heretofore known to use topical anesthetics in combination with organic nitrates for treatment of anal diseases.

OBJECTS OF THE INVENTION

It is the object of the invention to provide a treatment for anal disease, such as anal fissure, anal ulcer, hemorrhoidal disease, or levator spasm.

It is also an object of the invention to provide a method of treating anal fissure, anal ulcer, hemorrhoidal disease, and levator spasm whereby the affected areas are contacted with an effective amount of nitric oxide delivered by release from an organic nitrate.

It is a further object of the invention to provide a treatment for anal fissure, anal ulcer, hemorrhoidal disease, and levator spasm whereby the affected areas are contacted with an effective amount of nitric oxide delivered by release from an organic nitrate in combination with a corticosteroid.

It is yet further an object of the invention to provide a treatment for anal fissure, anal ulcer, hemorrhoidal disease, and levator spasm whereby the affected areas are contacted with an effective amount of nitric oxide delivered by release from an organic nitrate in combination with a topical anesthetic.

It is yet further an object of the invention to provide a treatment for anal fissure, anal ulcer, hemorrhoidal disease, and levator spasm that is more effective than treatments heretofore known.

This and other objects of the invention will become more apparent in the discussion below.

DETAILED DESCRIPTION OF THE INVENTION

The present invention concerns a treatment directed at the underlying cause of anal disease, such as anal fissure, anal ulcer, hemorrhoidal disease, or levator spasm, namely, an unidentified abnormality of the internal anal sphincter muscles. The treatment according to the invention comprises application of an effective amount of nitric oxide donor to afflicted tissue, in a suitable topical or suppository, physiologically acceptable carrier. The nitric oxide donor is preferably an organic nitrate such as nitroglycerin, i.e., glyceryl trinitrate, ethylene glycol dinitrate, glyceryl 1,2-dinitrate, glyceryl 1,3-dinitrate, glyceryl 1-mononitrate, butane 1,2,4-triol nitrate, mannitol hexanitrate, pentaerythrityl tetranitrate, pentaerythrityl trinitrate, isosorbide dinitrate, isosorbide mononitrate, erythrityl tetranitrate, or other organic esters of nitric acid of the formula R—[C—O—NO$_2$]$_x$, where R is an alkyl, cycloalkyl, or alkenyl group having from 1 to 18 carbon atoms or an aromatic group having from 6 to 18 carbon atoms and where x is an integer of from 1 to 5, or a combination of two or more of the foregoing. Optionally, the medication may comprise a corticosteroid such as hydrocortisone, i.e., 17-hydroxycorticosterone, a topical anesthetic such as dibucaine, or both a corticosteroid and a topical anesthetic.

The nitric oxide donor will be present in the medication in a concentration from about 0.01% to 10% by weight, preferably from about 0.5% to 7% by weight, based upon the total weight of the medication. If nitroglycerin is the nitric oxide donor, the preferred concentration will be from about 0.01% to 5% by weight, based on the total weight of the preparation. A corticosteroid will be present in a concentration of from about 0.001% to 10% by weight, preferably from about 0.1% to 5% by weight, based upon the total weight of the medication. If hydrocortisone is the corticosteroid, the preferred concentration will be from about 0.5% to 2.5% by weight. The topical anesthetic will be present in a concentration of from about 0.1% to 5% by weight, preferably from about 0.5% to 4% by weight, based upon the total weight of the medication. If dibucaine is the topical anesthetic, the preferred concentration is from about 0.5% to 2% by weight.

The compositions of the present invention may be formulated into highly convenient dosage forms with thickening agents, including thickened solutions or lotions, ointments (including creams and gels), and the like.

Thickened solutions or lotions and ointments may be formed by incorporating with the active ingredients, various gelling agents or other thickeners (viscosity increasers) which permit release of the active ingredients to the skin or tissue upon application. These forms are advantageously employed to lessen the runoff from the skin or tissue that may occur with the more fluid composition forms. Importantly, they also permit more sustained contact of the penetration enhancer with the treated surfaces, thus enhancing the speed of delivery of the active ingredients subcutaneously, and providing more accurate and controllable dosing. Accidental spilling and undesired contact with the material can also be minimized with these types of formulations.

It is advantageous to use water-dispersible thickening agents (i.e., agents dispersible in water to form a homogeneous distribution or solution), such as the polyethylene glycols, as they are readily compatible with water or other diluents to be formulated in the compositions. Alternatively, an emulsion base may be used to impart the desired thickening effect, together with the emollient effect of the lipoid phase of the emulsion base.

The water-soluble thickening bases may use polyethylene glycols of different viscosities, dependent upon the desired consistency and concentration of active ingredients to be incorporated into the compositions. Other thickening agents include water-dispersible gums, carboxyvinyl polymers, methyl cellulose, sodium carboxymethyl cellulose, alginates, and the like.

Lotions and ointments incorporating emulsion bases may contain the usual ingredients to provide the base, including fatty alcohols such as acetyl alcohol, an emulsifier such as lauryl sulfate, and water. Also, the remainder of a topical preparation may comprise one or more conventional ointment components selected from the group consisting of white petrolatum, lanolin, distilled water, and mineral oil, in conventional amounts. The remainder of a suppository may comprise conventional amounts of conventional suppository components such as zinc oxide and/or cocoa butter.

Pourable pharmaceutical dosages may be provided and dispensed in graduated containers, or containers which contain a given volume, such as 5 cc or the like. Containers with columns of 20 cc and above provide convenient multiple dosage forms, and those containing a typical single dose, such as from about 05.g to about 10 grams of a combination of active ingredients, provide convenient dosage forms. Squeeze tubes for lotions and ointments and cotton stick applicators may all be used for topical application of the thickened compositions.

The compositions of the present invention can also be administered by spraying and misting such as from misting devices and aerosol bottles, which containers are charged with fluid formulations containing at least 10% by weight of a combination of active ingredients, along with an aqueous diluent and, optionally, thickening agents, physiological salts, and the like. These compositions can be administered as either liquids or semisolid gels or mousses, dependent upon the amount of gelling agents or surfactants included in the compositions. Compositions for this purpose are sufficiently fluid to permit dispensing by spray or mist from the container, and also meet the previously described criteria for penetrability.

In treatment according to the invention, from about 500 to 1000 mg of ointment is applied topically to the external anus and to the distal anal canal with the finger or an applicator. Optionally, the medication can be delivered intra-rectally as a 2–3 gm suppository. The medication is applied in this fashion three or more times daily in the case of the ointment or once or more times daily in the case of the suppository.

The invention can perhaps be better appreciated by referring to the following examples:

EXAMPLES

Example 1

An ointment according to the invention was prepared by admixing 12.5 gm of 2% by weight nitroglycerin in white petrolatum, lanolin, and distilled water (nitroglycerin ointment, USP 2%; E. Fougera & Co., Melville, N.Y.) with 37.5 gm white petrolatum, USP (VASELINE®; Chesebrough-Ponds USA Co., Greenwich, Conn.) in a laboratory mixing vessel at room temperature. The resulting mixture comprised 50 gm of a 0.5% nitroglycerin ointment.

Example 2

An ointment comprising 12.5 gm of 2% nitroglycerin in white petrolatum, lanolin, and distilled water (nitroglycerin ointment, USP 2%; E. Fougera & Co., Melville, N.Y.) was admixed with 20 gm. of 2.5% by weight hydrocortisone in white petrolatum and light mineral oil (hydrocortisone ointment USP 2.5%; Clay-Park Labs, Inc., Bronx, N.Y.), and with 17.5 gm of white petrolatum USP (VASELINE®; Chesebrough-Ponds USA Co., Greenwich, Conn.) in a laboratory mixing vessel at room temperature. The resulting mixture comprised 50 gm of a 0.5% nitroglycerin and 1% hydrocortisone ointment.

Example 3

An ointment comprising 12.5 gm of 2% nitroglycerin by weight in white petrolatum, lanolin, and distilled water (nitroglycerin ointment, USP 2%; E. Fougera & Co., Melville, N.Y.) was admixed with 25 gm of 1% by weight dibucaine USP in white petrolatum, light mineral oil, acetone sodium bisulfite, lanolin, and purified water (NUPERCAINAL®; Ciba Consumer Pharmaceuticals, Edison, N.J.), and with 12.5 gm of white petrolatum USP (VASELINE®; Chesebrough-Ponds USA Co., Greenwich, Conn.) in a laboratory mixing vessel at room temperature. The resulting mixture comprised 50 gm of a 0.5% nitroglycerin and 0.5% dibucaine ointment.

Example 4

An ointment comprising 2.5 gm of 2% nitroglycerin in white petrolatum, lanolin, and distilled water (nitroglycerin ointment, USP 2%; E. Fougera & Co., Melville, N.Y.) was admixed with 20 gm. of 2.5% by weight hydrocortisone in white petrolatum and light mineral oil (hydrocortisone ointment USP 2.5%; Clay-Park Labs, Inc., Bronx, N.Y.), and with 25 gm. of 1% by weight dibucaine USP in white petrolatum, light mineral oil, acetone sodium bisulfite, lanolin, and purified water (NUPERCAINAL®; Ciba Consumer Pharmaceuticals, Edison, N.J.), and with 2.5 gm of white petrolatum USP (VASELINE®; Chesebrough-Ponds USA Co., Greenwich, Conn.) in a laboratory mixing vessel at room temperature. The resulting mixture comprised 50 gm of a 0.1% nitroglycerin, 1% hydrocortisone, and 0 5% dibucaine ointment.

Example 5

A 29 year old female had a seven day history of anal pain and bleeding with bowel movements. Physical exam showed posterior midline anal fissure. The patient rated her pretreatment pain 7/10. The patient applied approximately 500 mg of the ointment prepared in Example 1, three times daily and after bowel movements. The patient reported that her pain was gone following initial application. After two weeks of treatment the fissure had healed completely.

Example 6

A 40 year old female had a three-month history of anal pain and bleeding with bowel movements. Physical examination showed a superficial posterior midline anal fissure. The patient rated her pre-treatment pain 7/10. The patient applied approximately 500 mg of the ointment prepared in Example 1, three times daily and after bowel movements. After one week of treatment the patient noted persistent bleeding, but her pain was rated 2/10. After three weeks of treatment, the fissure was healed, and pain was gone.

Example 7

A 36 year old man had a two year history of anal pain and bleeding with bowel movements. Exam showed a posterior midline anal ulcer. Pretreatment pain was rated 9/10. The patient was treated with HC/pramoxine cream (Analpram-HC® 2.5%; Ferndale Laboratories, Inc., Ferndale, Mich.) three times daily and following bowel movements. After one week of treatment the patient rated his pain 6/10, and the physical condition was essentially unchanged. The patient was then treated with approximately 500 mg of the ointment prepared according to Example 2, three times daily and after bowel movements. He reported "immediate" relief of pain with each application. After one week of such therapy the ulcer was smaller, but not yet completely healed.

Example 8

A 23 year old female had a one-month history of anal pain and bleeding with bowel movements. Exam showed a superficial, posterior midline anal fissure. She had previously failed a course of hydrocortisone therapy. Pretreatment pain was rated 9/10. The patient was treated with approximately 500 mg of the preparation of Example 1, three times daily and after bowel movements. After one week of treatment the fissure was still present. Pain was then rated 8/10. The patient was treated with approximately 50 mg of the preparation of Example 2, three times daily and after bowel movements. Following one week of therapy with the second ointment the patient reported no pain and no bleeding. Subsequent examination showed that the fissure had healed.

Example 9

A 27 year old female had a three day history of anal pain and bleeding with bowel movements. Physical examination showed a superficial anterior midline anal fissure. Pretreatment pain was rated 4/10. The patient was treated with the preparation of Example 2, approximately 500 mg three times daily and after bowel movements. Following one week of therapy the patient reported that her pain had diminished to 2/10. Exam showed improvement. After another fifteen day's of therapy, the patient was pain free and the fissure had healed.

Example 10

A 27 year old man presented with a five day history of anal pain. Physical examination revealed a 1 cm thrombosed external hemorrhoid in the left anterolateral anal quadrant. The patient was treated with the preparation of Example 3, approximately 500 mg three times daily and after bowel movements. He reported a significant reduction in anal pain and throbbing three days later.

Example 11

A 57 year old man was referred for treatment of documented levator spasm which developed following lower spinal surgery two years before. The patient was treated with the preparation of Example 1, approximately 500 mg. intra-anally three times daily and after bowel movements. He reported improvement of the anorectal spasm within one day. Treatment was then switched to the preparation of Example 3, approximately 500 mg. intra-anally three times daily and after bowel movements. Pain relief was not as great, and the preparation of Example 1 was restarted.

The proceeding specific embodiments are illustrative of the practice of the invention. It is to be understood, however, that other expedients known to those skilled in the art or disclosed herein may be employed without departing from the spirit of the invention or the scope of the appended claims.

I claim:

1. A method of treating an anal fissure present in an anal canal of a patient, comprising topically administering to the anal canal of the patient a preparation comprising an effective amount of a nitric oxide donor.

2. The method of claim 1, wherein the nitric oxide donor is an organic nitrate.

3. The method of claim 2, wherein the organic nitrate is selected from the group consisting of nitroglycerin, ethylene glycol dinitrate, glyceryl 1,2-dinitrate, glyceryl, 1,3-dinitrate, glyceryl 1-mononitrate, butane 1,2,4-triol trinitrate, mannitol hexanitrate, pentaerythrityl tetranitrate, pentaerythrityl trinitrate, isosorbide dinitrate, isosorbide mononitrate, and erythrityl tetranitrate.

4. The method of claim 3, wherein the organic nitrate is nitroglycerin.

5. The method of claim 1, wherein the preparation comprises from about 0.1% to 10% by weight of nitric oxide donor, based upon the total weight of the preparation.

6. The method of claim 1, wherein the preparation comprises an effective amount of a corticosteroid.

7. The method of claim 6, wherein the corticosteroid is hydrocortisone.

8. The method of claim 6, wherein the preparation comprises a corticosteroid in an amount of from about 0.5% to 2.5% by weight, based upon the total amount of the preparation.

9. The method of claim 1, wherein the preparation comprises an effective amount of a topical anesthetic.

10. The method of claim 9, wherein the topical anesthetic is dibucaine.

11. The method of claim 9, wherein the preparation is comprised of topical anesthetic in an amount of from about 0.5% to 2% by weight, based upon the total weight of the preparation.

12. The method of claim 1, wherein the preparation comprises one or more pharmaceutically acceptable carriers or excipients in admixture or otherwise in association with said nitric oxide donor.

13. The method of claim 12, wherein the exicipients comprise one or more excipients selected from the group consisting of white petrolatum, mineral oil, lanolin, distilled water, acetone sodium bisulfite, zinc oxide, and cocoa butter.

14. The method of claim 12, wherein the preparation is an ointment.

15. The method of claim 12, wherein the preparation is a suppository.

16. The method of claim 1, wherein the preparation is applied to the anal canal at least one time daily.

17. The method of claim 16, wherein the preparation is applied to the anal canal from 2 to 8 times daily.

18. A method of treating hemorrhoids present in an anal canal of a patient, comprising topically administering to the anal canal of the patient a preparation comprising an effective amount of a nitric oxide donor.

19. The method of claim 18, wherein said nitric oxide donor is selected from the group consisting of nitroglycerin, ethylene glycol dinitrate, glyceryl, 1,2-dinitrate, glyceryl 1,3-dinitrate, glyceryl 1-mononitrate, butane 1,2,4-triol trinitrate, mannitol hexanitrate, pentaerythrityl tetranitrate, pentaerythrityl trinitrate, isosorbide dinitrate, isosorbide mononitrate, and erythrityl tetranitrate.

20. The method of claim 18, wherein said nitric oxide donor is nitroglycerin in an amount of 0.01% to 5% by weight, based on the total weight of the preparation.

21. A method of treating an anal disorder selected from one or more of the group consisting of anal fissure, anal ulcer, hemorrhoidal disease, and levator spasm and ameliorating pain associated therewith, comprising topically administering to an anal canal of a patient having such a disorder a preparation comprising an effective amount of a preparation comprising an effective amount of a nitric oxide donor.

22. The method of claim 21, wherein said nitric oxide donor is selected from the group consisting of nitroglycerin, ethylene glycol dinitrate, glyceryl 1,2-dinitrate, glyceryl 1,3-dinitrate, glyceryl 1-mononitrate, butane 1,2,4-triol trinitrate, mannitol hexanitrate, pentaerythrityl tetranitrate, pentaerythrityl trinitrate, isosorbide dinitrate, isosorbide mononitrate, and erythrityl tetranitrate.

23. The method of claim 22, wherein said anal disorder is anal fissure or ulcer.

24. The method of claim 22, wherein said anal disorder is hemorrhoidal disease.

25. The method of claim 22, wherein said anal disorder is levator spasm.

26. The method of claim 21, wherein said nitric oxide donor is nitroglycerin in an amount of 0.01% to 5% by weight, based on the total weight of the preparation.

* * * * *